US00PP12783P2

(12) United States Plant Patent
Lyrene

(10) Patent No.: US PP12,783 P2
(45) Date of Patent: Jul. 16, 2002

(54) BLUEBERRY PLANT NAMED 'WINDSOR'

(75) Inventor: Paul M. Lyrene, Gainesville, FL (US)

(73) Assignees: Thomas D. Stadsklev; Florida Foundation Seed Producers, Inc., both of Greenwood, FL (US)

( * ) Notice: Subject to any disclaimer, the term of this patent is extended or adjusted under 35 U.S.C. 154(b) by 0 days.

(21) Appl. No.: 09/698,650

(22) Filed: Oct. 30, 2000

(51) Int. Cl.[7] ..... A01H 5/00
(52) U.S. Cl. ..... Plt./157
(58) Field of Search ..... Plt./157, 156

*Primary Examiner*—Bruce R. Campell
*Assistant Examiner*—June Hwu

(57) ABSTRACT

A new and distinct low-chill tetraploid highbush blueberry (Vaccinium) variety of complex hybrid ancestry, based largely on *V. corymbosum* with some genes of *V. darrowi*. Its novelty consists of the following unique combination of features:

1. Produces a vigorous bush that is upright but somewhat spreading.
2. Has high resistance to cane canker (*Botryosphaeria corticis*) and medium resistance to stem blight (*B. dothidia*) and phytophthora root rot *Phytophthora cinnamomi*).
3. Flowers and fruits well in areas of central and north Florida where the mean temperature of the coldest month is 60° F. or colder.
4. Ripens its fruit 60 days after flowering in north-central Florida (latitude 29.5).
5. Ripens 80% of its fruit between April 10 and May 5 in north-central Florida.
6. Produces berries that are very large, firm, dark-blue in color, have a large and sometimes humid picking scars, and a sweet, pleasant flavor.
7. Propagates readily from softwood cuttings.

3 Drawing Sheets

ORIGIN OF THE VARIETY

'Windsor' originated as a seedling from the cross FL83-132×'Sharpblue', made in 1984 in a greenhouse in Gainesville, Fla. Neither parent is patented. FL83-132 was an advanced selection from the Florida blueberry-breeding program and 'Sharpblue' is an unpatented cultivar released by the University of Florida in 1975. Based on large fruit size and quality, 'Windsor' was selected along with 500 other seedlings from a population of about 10,000 hybrid seedlings evaluated in the field during the fruiting season of 1985. After being observed during the fruiting seasons of 1987 and 1988, 'Windsor' was propagated by softwood cuttings in May 1988, and an 8-plant plot was planted at the University of Florida Horticultural Research Unit in Gainesville in January 1992. In 1992, more 'Windsor' plants were propagated by cuttings, and 10 plants were planted at each of 8 sites in north and central Florida. In 1996 and 1997, several thousand 'Windsor' plants were planted in beds of pine bark in a field at Windsor, Fla., near Gainesville. Based on high yields, early ripening, and large berries in these test plots, a decision was made to propagate 'Windsor' as a commercial cutivar.

ASEXUAL PROPAGATION OF THE VARIETY

'Windsor' has been propagated by rooting softwood cuttings under mist on numerous occasions in Gainesville, Fla. (Alachua County). In every case, all resulting plants have displayed the characteristics of the variety.

DESCRIPTION OF THE VARIETY

Figure 1:
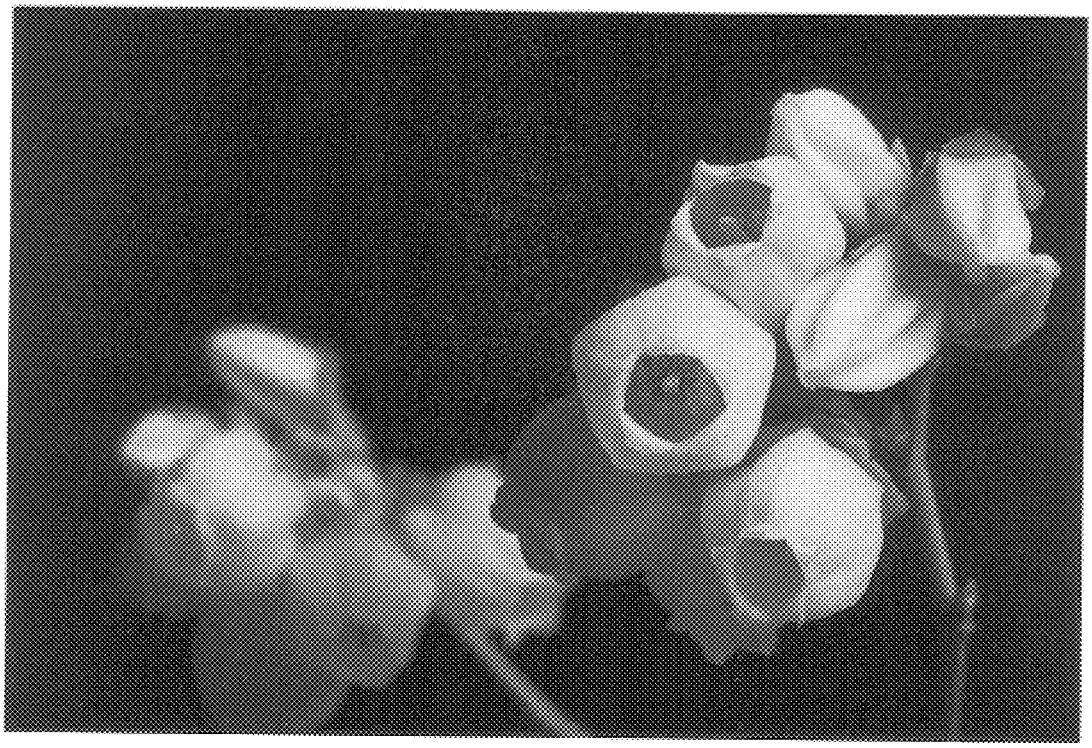
FIG. 1 shows the flower cluster of 'Windsor' and illustrates the shape of the flower and the wide corolla aperture.
Figure 2:
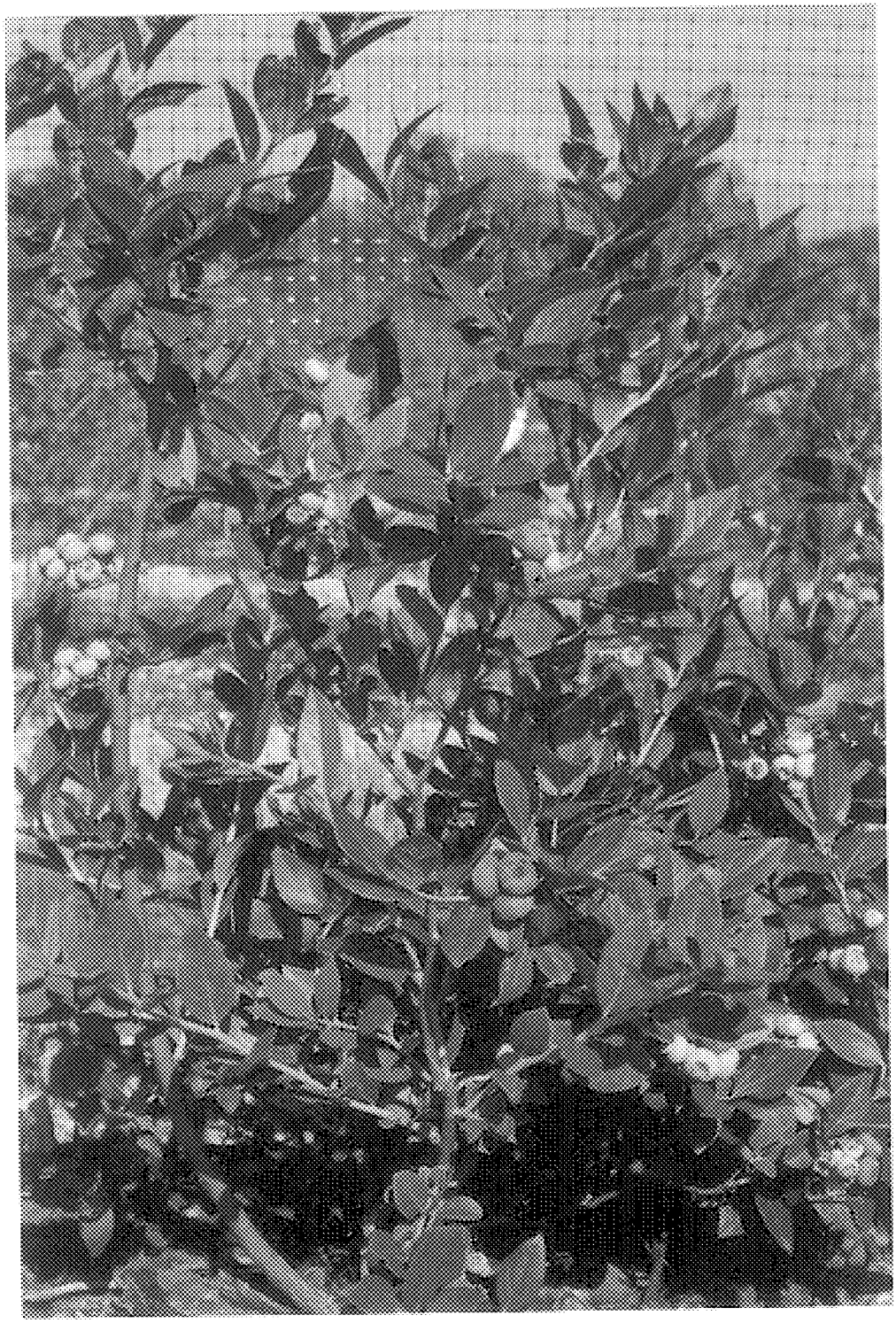
FIG. 2 shows a plant in late April in north Florida, illustrating the semi-upright growth habit and the vigorous spring shoots.
Figure 3:
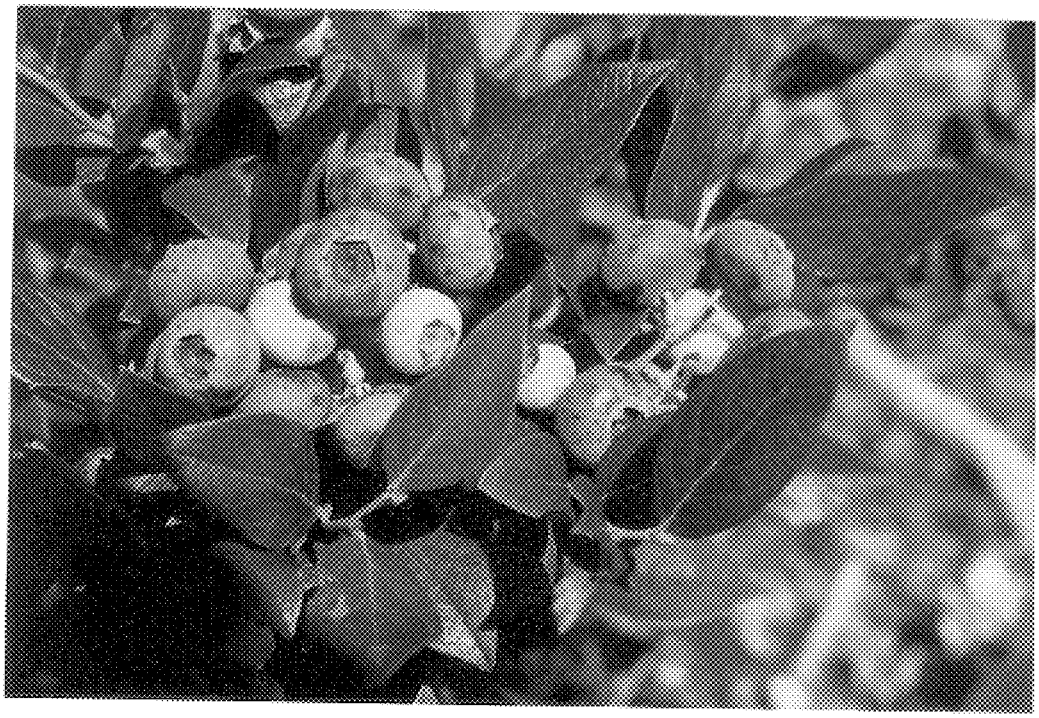
FIG. 3 shows in closer view, the ripe and unripe fruit of 'Windsor', illustrating the wide calyx aperture and the relatively undeveloped calyx lobes.

The following is a detailed botanical description of 'Windsor', its flowers, fruit and foliage, based on observation of specimens grown in the field in Windsor, Fla. near Gainesville. Color descriptions, except those given in common terms, use terminology from "The Pantone Book of Color" by Leatrice Eiseman and Lawrence Herbert; Harry N. Abrams, Inc. Publishers, New York. Because the color reproductions in the drawings are inexact due to limitations of the film, the Pantone colors should be considered correct even when they differ from the colors in the drawings.

Bush: Bush size is reported for two-year-old plants that had been propagated from softwood cuttings and had been planted into a bed of pine bark in a field in Windsor, Fla. The bed was provided with overhead irrigation and was managed like a commercial blueberry planting in Florida.

*Plant height.*—110 cm.

*Canopy diameter.*—105 cm.

*Plant vigor.*—High, about equal to 'Sharpblue', 'Gulf Coast', and 'O'Neal' (all not patented).

*Growth habit.*—Between upright and spreading.

*Flower bud number compared to other Florida cultivars.*—Medium.

*Cold hardiness.*—Except for the flowers and fruit, some of which have been killed in some years by freezes in February and March, 'Windsor' has not suffered freeze damage to the bush in Gainesville. Dormant plants have withstood temperatures of 18° F. without damage.

*Chilling requirement.*—Based on the time and extent of spring vegetative growth and flower bud break in Gainesville, 'Windsor' appears to have a chilling requirement of about 300 hours below 45° F. after the plants have become dormant in the winter.

*Productivity.*—Large plants on good soil have yielded 5 to 6 pounds per plant per year after 3 to 4 years in the field.

*Suckering tendency.*—Medium to high, with 3–7 major canes from the base of 2-year-old plants.

*Texture of 2-year-old main canes.*—Rough, exfoliating.

*Color of 2-year-old rough bark.*—"Birch", Pantone 13-0905.

Twigs:

*Color of smooth shoots from previous year's spring flushes, viewed Mar. 2, 2000.*—"Mustard Gold", Pantone 16-1133.

*Color of smooth shoots from previous year's late-summer flushes, viewed Mar. 2, 2000.*— "Mustard Gold", Pantone 16-1133.

*Internode length.*—1.3 cm on strong upright shoots.

Characteristics of mature leaves:

*Leaf length excluding petiole.*—Typically 60 to 65 mm, but can reach 90 mm on vigorous shoots.

*Leaf width.*—Typically 30 to 35 mm but can reach 45 mm on vigorous shoots.

*Leaf shape.*—Oval to Lanceolate.

*Leaf tip.*—Acuminate.

*Leaf margin.*—Entire.

*Color of upper surface.*—A shade of green called "Cypress", Pantone 18-0322.

*Color of lower surface.*—A shade of green called "Peridot", Pantone 17-0336.

*Pubescence, upper surface of leaf.*—Glabrous.

*Pubescence, lower surface of leaf.*—Glabrous.

*Pubescence on the leaf margin.*—None.

*Synchrony of leafing and flowering.*—Plants usually begin leafing at about the same time as lowering when grown in north Florida.

Flowers:

*Fragrance.*—Slight camellia fragrance.

*Flower cluster: (tight, medium, or open).*—Medium.

*Average number of flowers per cluster.*—3–7, mostly 3–6.

*Inflorescence: pedicel length.*—5–6 mm.

*Peduncle length.*—8–13 mm, mostly about 11 mm.

*Corolla length from pedicel attachment point to the corolla tip.*—11.8 mm.

*Diameter of corolla tube at widest point.*—9.0 mm.

*Corolla aperture diameter.*—4.8 mm.

*Corolla color at anthesis during mild weather.*—"Snow White", Pantone 11-0602.

*Corolla color 6 days before anthesis on flower parts fully exposed to sun.*—"Moonlite Mauve", Pantone 16-2614. Stamens and pistils typical for highbush blueberry.

*Pollen abundance.*—Abundant.

*Pollen staining with acetocarmine.*—99.3% of the grains stain. This indicates potentially high male fertility.

*Average date by which the first 50% of the flowers have opened in Gainesville, Fla.*—February 21.

*Self-compatibility.*—Above-average self-fruitfulness for a Florida southern highbush blueberry. In one test, 94 flowers hand self-pollinated in a greenhouse produced 68 ripe berries (72%). These were about 75% of the size of cross-pollinated berries and were delayed in ripening by only about 7 days compared to berries from cross-pollination.

Berry:

*Weight.*—Leader berries on young plants: 2.48 g per berry.

*Berry height.*—12 mm.

*Berry width.*—17 mm.

*Diameter of the calyx aperture on mature berry.*—7 mm.

*Berry surface color, ripe on the plant.*—"Zinc", Pantone 17-2601.

*Berry surface color with wax removed.*—"Slate Black", Pantone 19-0814.

*Interior flesh color of mature berry.*—"Frozen Dew", Pantone 13-0513.

*Color of washed, dried seeds.*—"Glazed ginger", Pantone 18-1154 (a shade of brown).

*Surface wax.*—Below-average resistance to rubbing off compared to other southern highbush cultivars.

*Pedicel scar.*—Medium to large; picking the berry sometimes tears the skin.

*Berry firmness.*—High.

*Berry flavor.*—Sweet, sub acid.

*Berry fragrance.*—None.

*Berry texture.*—Good; thin skins, small seeds, and inconspicuous sclereids.

*Maturity.*—Date when the first 50% of the crop is ripe on 'Windsor' averages April 22 in Gainesville compared to April 27 for Star (U.S. Plant Pat. No. 10,675) and May 1 for Sharpblue (unpatented).

Diseases, insects, and mites:

*Cane canker resistance.*—Highly resistant.

*Dieback due to stem blight.*—Moderately resistant.

*Phytophthora root rot.*—Moderately resistant.

*Fungal leaf spots.*—Above-average resistance.

*Blueberry bud mites.*—Resistant.

Ease of propagation: Roots readily from softwood cuttings.

I claim:

1. A new and distinct highbush blueberry plant, substantially as illustrated and described, characterized by its vigorous, semi-upright bush, low chill requirements, and large, early-ripening fruit.

* * * * *